(12) United States Patent
Cewers

(10) Patent No.: US 6,448,791 B1
(45) Date of Patent: Sep. 10, 2002

(54) METHOD FOR ANALYZING ANAESTHETIC AGENTS AND AN ANALYZER OPERATING ACCORDING TO THE METHOD

(75) Inventor: Göran Cewers, Lund (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/550,112

(22) Filed: Apr. 14, 2000

(30) Foreign Application Priority Data

Apr. 27, 1999 (SE) ................................ 9901512

(51) Int. Cl.$^7$ ................................ G01R 27/26
(52) U.S. Cl. ................................ 324/663
(58) Field of Search ................ 324/674, 663, 324/658

(56) References Cited

U.S. PATENT DOCUMENTS 4,453,126 A  * 6/1984 Volgyesi ............... 324/663
5,134,381 A  7/1992 Schmitz et al.
5,804,974 A  9/1998 Brubaker et al.

FOREIGN PATENT DOCUMENTS

EP       0 924 513       8/1998

OTHER PUBLICATIONS

"Medicin Och Teknik," 4th Ed. (1995) pp. 472–480 Missing month.

* cited by examiner

*Primary Examiner*—N. Le
*Assistant Examiner*—James Kerveros
(74) *Attorney, Agent, or Firm*—Schiff Hardin & Waite

(57) ABSTRACT

In a method for analyzing anaesthetic agents and an analyzer operating according to the method, a parameter directly related to the anaesthetic agent's dielectric polarization is determined. A measuring unit has a container for the anaesthetic agent, two capacitor plates, devised so the anaesthetic agent can be interposed between them for analysis, a voltage source, connectable to the capacitor plates for controlled application of at least one voltage across the plates, and a voltmeter, connectable to the capacitor plates for measuring a voltage across the capacitor plates. The measurement results are analyzed in an analysis unit and the anaesthetic agent is identified from the analysis result. Mixing and/or contamination of anaesthetic agents can also be identified.

21 Claims, 4 Drawing Sheets

METHOD FOR ANALYZING ANAESTHETIC AGENTS AND AN ANALYZER OPERATING ACCORDING TO THE METHOD

BACKGROUND OF THE INVENTION

1. Field of the Invention

The present invention relates to a method for analyzing anaesthetic agents, suitable for identifying anaesthetic agents.

The present invention also relates to an analyzer for analyzing anaesthetic agents, suitable for identifying anaesthetic agents.

2. Description of the Prior Art

Anaesthetic agents are used for inducing anaesthesia and are administered to a patient in gaseous form. The anaesthetic agent is generally present in liquid form in a vaporizer and is vaporized into gaseous form therein. There are numerous anaesthetic agents. Desflurane, enflurane, halothane, isoflurane and sevoflurane are the most commonly used ones today. These agents are administered in different concentrations, and it is important that only one of them is administered at a time to a patient. Erroneous concentrations or a mixture of different anaesthetic agents could pose a risk to the patient. At worst, the patient could be seriously injured or even die. Liquid anaesthetics must also be handled with great care, since inhaling them at high concentrations is hazardous. Even long-term exposure to low concentrations of anaesthetic can pose risks to health. This is primarily a problem for hospital personnel.

Maintaining the most reliable conditions possible in the use of anaesthetic machines therefore is of the utmost importance.

Patients respond differently, however, to the aforementioned anaesthetic agents. One anaesthetic might evoke an allergic response in some patients, making it necessary to switch to another anaesthetic quickly.

One anaesthetic agent may be more suitable for use during the induction phase of anaesthesia but not during the remaining narcosis. One such anaesthetic agent is halothane, often used to anaesthetize children, since inspiring vaporized halothane is not unpleasant, but the agent could cause e.g. liver damage.

Most anaesthetic machines are therefore devised to enable the anaesthetist to switch to different anaesthetic agents relatively simply with no risk of simultaneously delivery of two different anaesthetic agents at the same time.

Different safety systems are also available. For example, special keyed connectors between respective gas bottles and vaporizers and/or color-coding when liquid anaesthetic in the vaporizer is replenished are used to prevent a mixture of anaesthetic agents in the vaporizer.

A disadvantage of these types of safety system is that they do not preclude human error. Residual anaesthetic in a vaporizer could, after use, be emptied by mistake into a container holding some other anaesthetic agent or be erroneously marked. Mixing would then occur the next time that an erroneously marked liquid is poured into a vaporizer.

The risk of this happening is greater than most people would believe. Anaesthetics are expensive, and many hospitals cannot afford to just throw away superfluous anaesthetic. Not all vaporizers are equipped with proper receivers for the keyed connectors. In these cases the keyed connector on the bottle is removed for filling the vaporizer.

Identification of the anaesthetic in a vaporizer and/or anaesthetic machine therefore provides for more reliable protection of the patient. Delivery can be stopped immediately if an erroneous anaesthetic agent is identified in the system.

Anaesthetic agents can be optically identified with absorption spectrophotometry from their respective refractive index, density, absorption in other materials, dielectric constant, etc.

A major problem encountered in anaesthetic identification is the similar chemical structures of different anaesthetic agents, resulting in similar properties. Several of the aforementioned methods usually require the use of highly specialized analysis equipment, or e.g. the concentration of the anaesthetic agent must be known. A number of these methods are also incapable of sensing mixtures of different anaesthetic agents. It is further not always possible, with the known methods, to detect contamination of or chemical changes in an anaesthetic agent.

Finding alternative methods and analyzers for analyzing and identifying anaesthetic agents in a simple, reliable and exclusive manner therefore is desirable, preferably with the ability to identify mixtures of different anaesthetic agents, contamination of anaesthetic agents and even chemical changes in an anaesthetic agent.

SUMMARY OF THE INVENTION

An object of the present invention is to provide a method for fast, simple and reliable analysis of anaesthetic agents, primarily for anaesthetic agents identification and for determination of changes in anaesthetic agents, especially mixing of different agents, contamination of an agent and chemical changes in an agent.

The above object is achieved in accordance with the principles of the present invention in a method for analyzing anaesthetic agents wherein at least one parameter that is directly related to dielectric polarization in an anaesthetic agent is determined, and the anaesthetic agent is analyzed (as to, for example, identity, mixture with other anaesthetic agents, contamination, etc.) dependent on the measured parameter directly related to dielectric polarization.

Dielectric polarization is a property of different materials caused by the polarization of molecules and atoms subjected to an electrical field. This polarization takes a certain amount of time and dissipates when the electrical field is removed. Thus, polarization reflects properties on the molecular and atomic level and is also completely independent of the dielectric constant. Since the effect depends on the movement of molecules and atoms, it is most pronounced in liquid and gaseous substances.

Measurements made of anaesthetic agents in liquid form have shown that they differ in their dielectric polarization. Anaesthetic agents therefore can be identified from their dielectric polarization or a parameter directly related to it. The differences are also sufficiently distinct for practical use.

Changes caused by fouling, mixing with other agents, chemical action and other factors, leading to a quantifiable change in the anaesthetic agent's dielectric polarization properties, can be determined with the method.

One advantageous way of identifying such a parameter is to sequentially expose the anaesthetic agent to different electrical fields. This creates a potential difference across the anaesthetic agent. A high-impedance voltmeter can then be used to measure the voltage component developing across the anaesthetic agent due to residual polarization. The voltage component is determined in relation to the created potential difference.

One way to create the potential difference is to short-circuit the electrical field during a time period.

The voltage/potential applied across the anaesthetic agent should be less than the electrochemical potential for the anaesthetic agent or components therein.

This determination can be made with greater precision if several measurements are performed with differing durations for the exposure to the electrical field.

Another way to increase identification precision, particularly when a large number of substances are to be identified, is to carry out determination of the parameter at different frequencies. A pattern "fingerprint" or spectrum then can be obtained for each anaesthetic agent, thereby increasing identification specificity. Pattern identification can be performed in a pattern recognition system or an artificial neural network and is iteratively taught to recognize pure anaesthetic agents and non-pure anaesthetic agents (contaminated agents, mixtures of different agents or chemically changed agents).

Other specific advantages are also achieved. When liquid anaesthetic in the vaporizer is identified, a relatively simple concentration meter of the known type can be arranged to measure the concentration of the anaesthetic agent in gaseous form. The simple concentration meter obtains information as to the identity of the anaesthetic agent, and appropriate scaling of the sensor signal from the concentration meter can then be performed.

Dielectric polarization can be determined in a number of ways in order to increase the specificity of qualitative analysis even further. A combination of different measurement methods can then result in a refined gradation of differences that cannot be achieved with a single measurement method.

Alternatively, a number of different parameters directly related to dielectric polarization can be determined and utilized in the same way.

The method can also be supplemented with determination of another property of the anaesthetic agent, e.g. molecular weight, absorption spectra etc. Merging different properties can then further increase specificity. This applies in particular to specify more precisely the degree of contamination, mixing, etc.

The above object is achieved in an analyzer according to the invention having a measuring unit for determining a parameter directly related to dielectric polarization and an analysis unit for performing the analysis based on the determined parameter.

As described above for the inventive method, the parameter can be a voltage component, and the measuring unit can then contain two conductive surfaces (e.g. capacitor plates), a voltage source and a voltmeter.

In accordance with the above, the measuring unit can also contain a short-circuiting circuit (to create the potential difference.)

In this embodiment, the voltage source can generate alternating currents across the entire frequency spectrum (including direct current). With this embodiment, a low-frequency method, i.e. more suitable for frequencies under e.g. 10 Hz, is mainly used. One particularly suitable frequency that yielded good results in experiments is around 1 Hz.

In an alternative version of the measuring unit for determining another parameter related to dielectric polarization, the measuring unit has two capacitor plates, an inductive load connected to an oscillatory circuit formed with the capacitor plates, a alternating current source, a voltmeter and a timer.

An applied voltage pulse, or train of voltage pulses, in the oscillatory circuit will decay, and the decay time is a measure of dielectric polarization. So activating the oscillatory circuit is sufficient for performing the determination. However, the design with an oscillatory circuit makes it possible to use higher frequencies advantageously. A high-frequency pulse is then applied to the oscillatory circuit. The pulse can advantageously exceed 30–40 MHZ.

Wireless communications for excitation and detection can be performed with EM waves when high-frequency waves are used.

The decay can be established from part of the actual decay curve that can be obtained.

Since the first embodiment can advantageously be used for lower frequencies and the second embodiment for higher frequencies, the embodiments can be combined in a single measuring unit for measurement over a broad frequency spectrum. It should be noted, however, that each of the two embodiments could be used over a wide frequency range.

DESCRIPTION OF THE PREFERRED EMBODIMENTS

Figure 1:
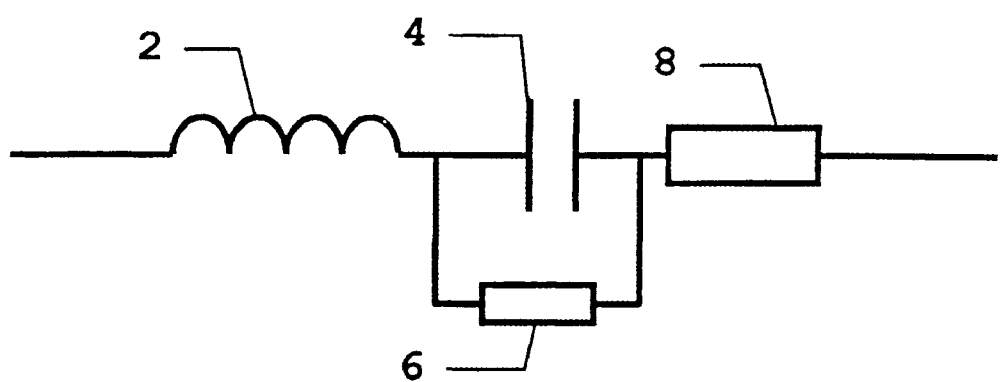
FIG. 1 shows an equivalent circuit for a capacitor for use in explaining the invention.

In reality, a capacitor does not consist of pure capacitance. FIG. 1 shows an equivalent circuit that reflects a model of a true capacitor. The equivalent circuit contains an inductance 2. A capacitance 4, in parallel with a first resistance 6, is in series with the inductance 2. A second resistance 8 is in series with these components.

The inductance 2 consists of inductance in lines and surface layers. The capacitance 4 corresponds to what is normally meant by a capacitor's capacitance, i.e.

$$C = \varepsilon \times \varepsilon_0 \times \frac{A}{d}$$

in which C is the capacitance, $\varepsilon_0$ is the dielectric constant for a vacuum, $\varepsilon$ is the dielectric's relative dielectric constant, A is the area of the capacitor plates and d is the distance between the capacitor plates. The first resistance 6 corresponds to the capacitor's leakage resistance, i.e. the dielectric's insulation. The second resistance 8 corresponds to resistance in the lines and surface layers and dielectric losses.

Of these, $\varepsilon$ and dielectric losses are variables in relation to frequency. Here, the variation is due to a large degree to the material in the dielectric. However, $\epsilon$ and dielectric losses are not mutually inter-dependent.

Figure 2:
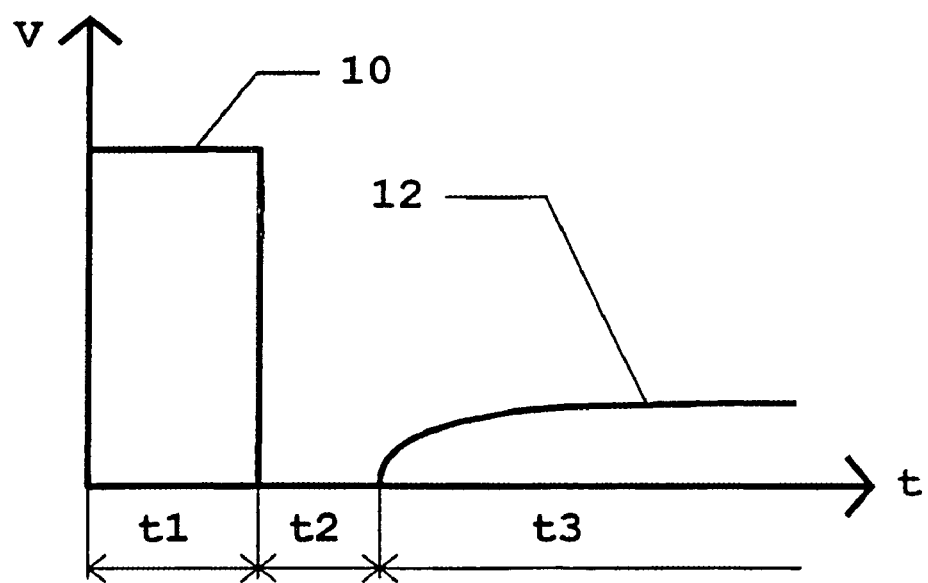
FIG. 2 is a diagram illustrating a first way to determine a parameter related to dielectric polarization in accordance with the invention.

FIG. 2 shows one way to achieve a measure of dielectric polarization. Dielectric polarization causes losses in the dielectric when it is exposed to an electrical field. Since polarization occurs with some inertia, it displays hysteresis of the kind occurring in e.g. iron cores in transformers.

The diagram in FIG. 2 shows voltage on the y-axis and time on the x-axis. A voltage 10 is applied across two capacitor plates (between which a liquid or gaseous anaesthetic agent can be arranged in some suitable fashion) to charge them during a first time period t1. The capacitor plates are briefly short-circuited during a second time period t2. The stored voltage then dissipates rapidly, however, polarization does not dissipate as rapidly. Since the dielectric (the anaesthetic agent in this instance) is polarized, a residual voltage 12 will develop across the capacitor plates. This residual voltage 12 can be quantified with a high-impedance voltmeter. The residual voltage 12 is a direct measure of polarization.

A better measure of polarization is obtained when this measuring procedure is performed several times with different durations of the first time period t1.

It should be repeated here that short-circuiting the capacitor plates actually only represents the creation of a potential difference compared to the voltage applied in the first time period t1 (short-circuiting is the application of a zero voltage). The voltage across the capacitor plates therefore initially (the first time period t1) be zero, and a negative voltage can be applied during the second time period t2. In principle, it is sufficient for the voltages during the first time period t1 and the second time period t2 to differ from each other. The second time period t2 is only used to change the capacitor charge into another potential and may not last long enough for any major change in the substance's dielectric polarization to occur.

In other words, just creating a potential difference between the first time period t1 and the second time period t2 is sufficient. It may be advantageous, however, for the first voltage to differ from zero when measurements are performed with different durations for the first time period t1.

One empirical study of liquid anaesthetic agents analyzed with this method found that the agents possess distinguishable dielectric polarization. Identifying anaesthetic agents from their dielectric polarization (or a parameter directly related thereto) is therefore feasible. This also applies to anaesthetic agents in gaseous and solid form.

Figure 3:
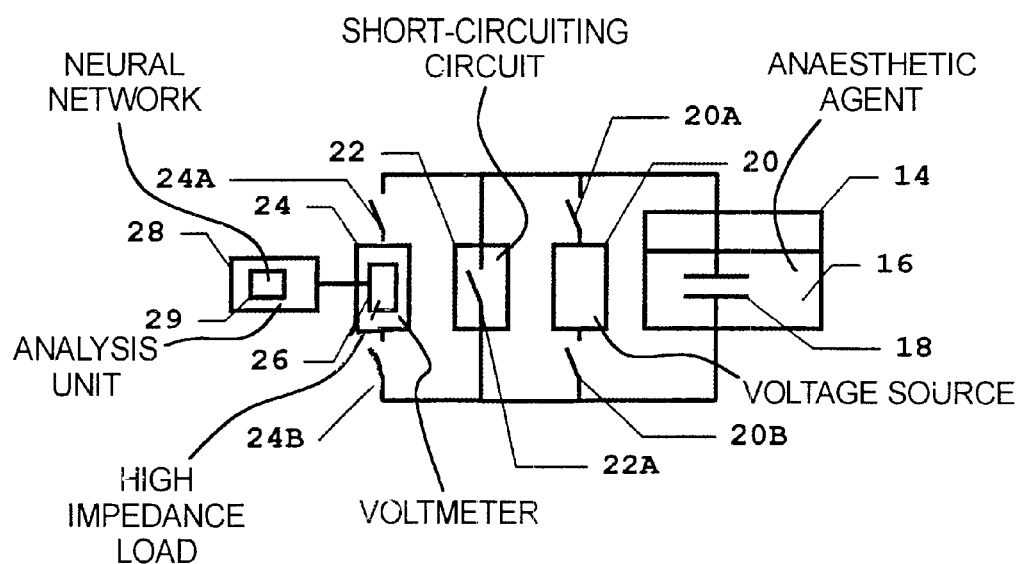
FIG. 3 shows a first embodiment of an analyzer according to the invention.

FIG. 3 shows a first embodiment of an analyzer according to the invention with a construction suitable for performing the method described above. Anaesthetic agents can be identified in this way.

An anaesthetic agent 16 can be placed in a container 14 for analysis. In this instance, the anaesthetic agent 16 is in liquid form. The liquid thus is also present between the two capacitor plates 18 (essentially forming a first conductive surface and a second conductive surface). The capacitor plates 18 are connectable to a voltage source 20 by switches 20A, 20B enabling the capacitor plates 18 to be charged.

A short-circuiting circuit 22, connectable to the capacitor plates 18 by a switch 22A and parallel to the voltage source 20, is provided to discharge the capacitor plates 18 during the second time period.

A voltmeter 24 with a high-impedance load 26, connected in parallel with both the voltage source 20 and short-circuiting circuit 22, is connectable to the capacitor plates 18 by switches 24A, 24B to measure a voltage component across the capacitor plates 18 after short-circuiting. The voltage component in this instance is a residual voltage across the capacitor plates 18, since they have been short-circuited. If another voltage is applied across the capacitor plates 18, the voltage component is a relative departure from the applied voltage.

The measurement signal from the voltmeter 24 is sent to an analysis unit 28 for identification of the anaesthetic agent 16 in the container 14.

If measurements are made at different frequencies, a more specific pattern can appear for each anaesthetic agent. The identity of the anaesthetic agent can then be determined in an artificial neural network 29 in the analysis unit 28. Of course, other pattern recognition system and analysis techniques can also be used.

In the inventive method and analyzer it is not only possible to identify different anaesthetic agents but also to determine purity of the anaesthetic agent, i.e. whether the agent is contaminated, mixed or chemically changed.

The switches 20A, 20B, 22A, 24A, 24B shown in FIG. 3 (indicating the connectability of the various components) can be controlled from the analysis unit 28 to connect the respective component for a specific period of time. The analysis unit 28 can also control the frequency and voltage from the voltage source 20 when it is connected to the capacitor plates 18. This control can be exercised in the way familiar to those skilled in the art and does not require any detailed description in this context.

Figure 4:
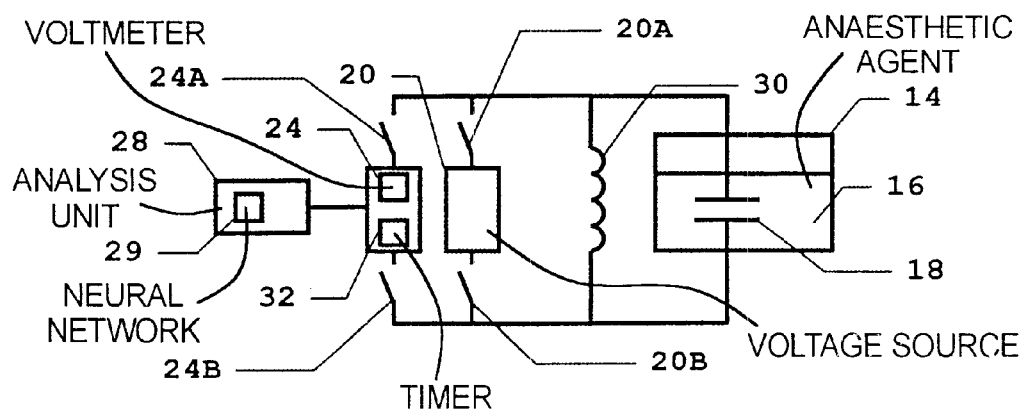
FIG. 4 shows a second embodiment of an analyzer according to the invention.

The same can be said about corresponding details in the second embodiment of the analyzer according to the invention as shown in FIG. 4. Identical parts and components have been assigned the same designations as in FIG. 3.

A container 14 holds liquid anaesthetic 16. Two capacitor plates 18 are also in the container 14.

A coil 30 is connected to the capacitor plates 18 to form an oscillatory circuit. A voltage source 20 is connectable to this oscillatory circuit by switches 20A, 20B. In this instance, the voltage source 20 is regulated to deliver alternating current. The voltage source 20 can be made to deliver a short pulse or a train of pulses to the oscillatory circuit.

A voltmeter 24 and a timer 32, connected in parallel to the voltage source 20, are connectable by switches 24A, 24B. An analysis unit 28 can use them to determine decay for the pulse in the oscillatory circuit. The decay depends on dielectric polarization and therefore constitutes a direct measure of it.

Figure 5:
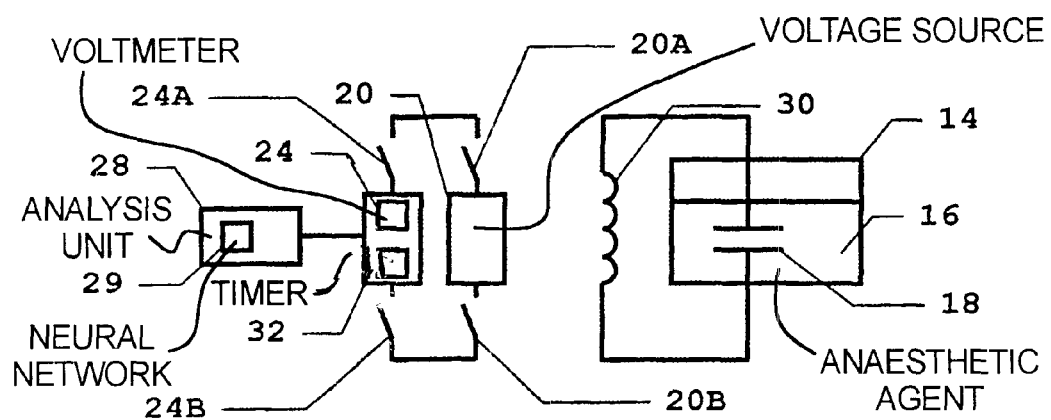
FIG. 5 shows a further version of the second embodiment of an analyzer according to the invention.

FIG. 5 shows a further version of the embodiment in FIG. 4. The same designations have been used here. The only difference is that the oscillatory circuit 18, 30 in the version according to FIG. 5 only utilizes a high-frequency measurement method and wireless communications by EM waves to excite and detect events. Wireless communications can be performed via an antenna (not shown in FIG. 5) or any other known means for wireless communication.

Figure 6:
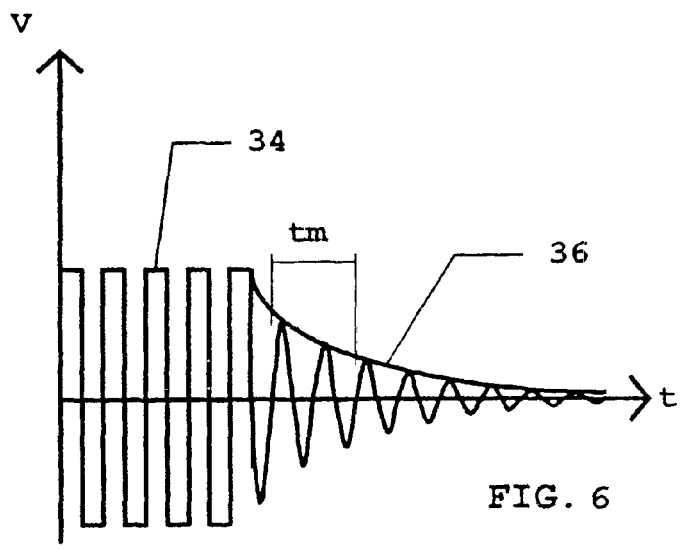
FIG. 6 is a diagram illustrating a second way to determine a parameter related to dielectric polarization in accordance with the invention.

This is shown more clearly in FIG. 6 which is a diagram depicting the way in which a train of voltage pulses 34 according to the above is applied and the way in which decay 36 occurs after the train of voltage pulses. Decay can be determined during a time period tm. In principle, the time constant for the decay is related to dielectric polarization.

The analysis unit 28 (FIG. 4) can contain an artificial neural network 29 for measuring decay for a number of different frequencies.

It should be noted that the above embodiments primarily depict advantageous designs for the analyzer according to the invention for a specific measurement situation. Anaesthetic interposed between the capacitor plates 18 does not need to be in liquid form either. The anaesthetic agent, in gaseous or liquid form can even be absorbed in or adsorbed onto a bearer arranged between the capacitor plates (or in a container between the capacitor plates). Even anaesthetic agents in solid form are possible, although not practical under normal circumstances of usage.

Figure 7:
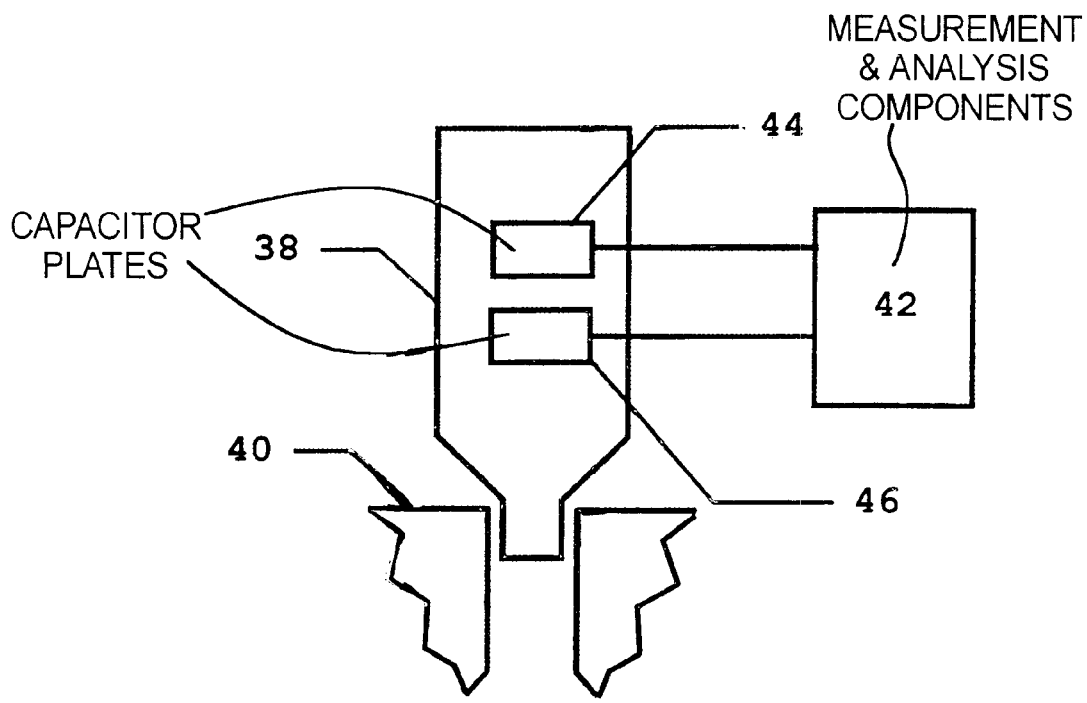
FIG. 7 shows a third embodiment of an analyzer according to the invention.

It is not necessary for the capacitor plates to come into physical contact with the anaesthetic agent. This is exemplified by a third embodiment of the analyzer, shown in FIG. 7. Here a bottle 38 containing an anaesthetic agent is coupled to a receiving part 40 of a vaporizer. The analyzer has measurement and analysis components according to the above (here depicted as box 42). A first capacitor plate 44 and a second capacitor plate 46 are connected to the bottle 38. A voltage across the plates 44, 46 will create an electrical field within a portion of the bottle 38, thereby creating a polarization of the anaesthetic agent within the field. The bottle 38 preferably is made of a glass or plastic either having properties that will not influence the measurements at the selected frequencies or having well defined properties that can be compensated for in the analysis of the anaesthetic agent.

The container 14 can be a part of a completely separate analyzer or even be part of, or the entire, anaesthetic container in a vaporizer. As noted above, the container 14 also can hold gaseous anaesthetic.

The analyzer can include variations of the illustrated embodiments. In particular, the analyzer can hold all the agents described in the two embodiments for active determination across the entire frequency range. In this instance, the coil should also be encircled by a switch.

Polarization properties are present at all frequencies but can be pronounced to varying degrees for the different anaesthetic agents, depending on the frequency. Thus there are frequency intervals in which it is easier to identify the different anaesthetics. Two different frequency ranges were identified above, but experiments with other frequencies could, in principle, yield additional intervals. Measurement in a number of intervals would increase the possibility of identifying individual anaesthetic agents and quantifying mixtures of different anaesthetic agents or contamination. In principle, the greater the number of different anaesthetic agents in a mixture, the greater the number of different measurements required.

The capacitor plates do not necessarily need to be two opposing plates. The polarization effect (in the anaesthetic agent) develops when an electrical field is applied across the anaesthetic agent. The capacitor plates therefore only need to be devised so an electrical field applied across them polarizes an anaesthetic agent. Thus, the plates can be parallel to each other and have other designs than flat plates (i.e. they could be curved, spherical or shaped in any feasible form, nor need the plates have the same shape). It is further not necessary to limit the analysis to two plates, three or more can also be used, in parallel or in sequence-thereby enabling more variables to be measured for enhancing the specificity (such as amount of agent being exposed to electrical field, different distances between plates, etc).

Figure 8:
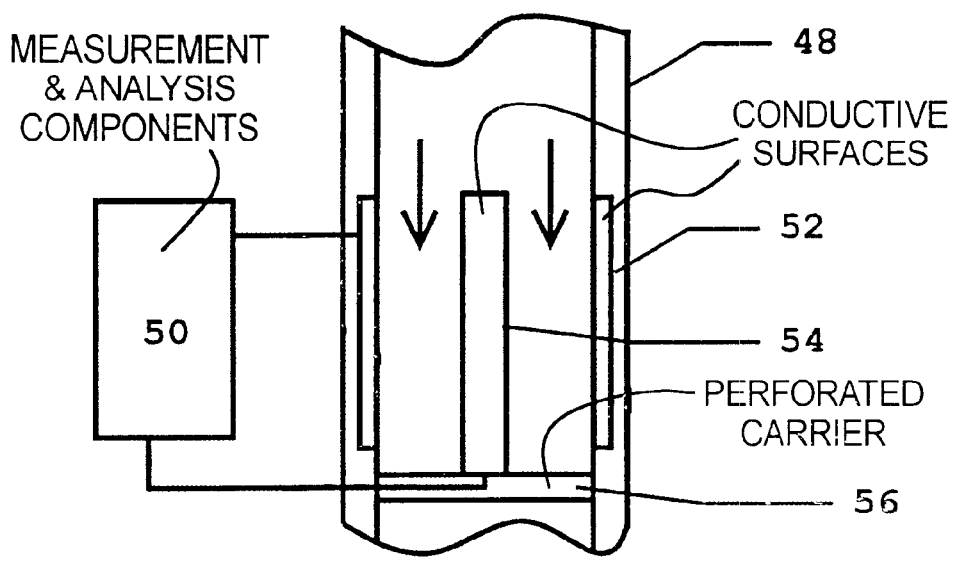
FIG. 8 shows a fourth embodiment of an analyzer according to the invention.

An example of differently shaped capacitor plates (or conductive surface) is shown in a fifth embodiment of the analyzer according to the invention in FIG. 8. Here, a tube 48 for transport of the anaesthetic agent 16 (into a vaporizer or to a vaporization point) is utilized. As in the fourth embodiment, the measuring and analyzing components are only depicted as a box 50. A first conductive surface 52 is achieved by a foil or similar arranged within the wall of the tube 48, thus providing a cylindrical shape. A second conductive surface 54 is achieved by a rod or cylinder arranged in the center of the tube (and thus also cylindrical in shape). A perforated carrier 56 keeps the second conductive surface 54 in place, while allowing the anaesthetic agent 16 to flow through it.

In a corresponding manner, determination of the voltage component across the plates to which voltage has been applied is not necessary either. Measuring the voltage across the polarized anaesthetic to determine dielectric polarization, and accordingly, to identify the anaesthetic agent, is also possible via other plates or in some other way.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for analyzing anaesthetic agents comprising the steps of:
    measuring at least one parameter of an anaesthetic agent directly related to dielectric polarization of said anaesthetic agent to obtain a measured parameter directly related to dielectric polarization; and
    analyzing said anaesthetic agent dependent on said measured parameter.

2. A method as claimed in claim 1 comprising measuring said parameter directly related to dielectric polarization by applying a first voltage across said anaesthetic agent for a first period of time, applying a second voltage across said anaesthetic agent for a second period of time to create a potential difference in said anaesthetic agent, and identifying a difference between said potential difference and said second voltage as said measured parameter directly related to dielectric polarization.

3. A method as claimed in claim 1 wherein the step of measuring said at least one parameter directly related to dielectric polarization comprises forming an oscillatory circuit in which anaesthetic agent is a component, applying a train of voltage pulses across said anaesthetic agent to induce oscillation in said oscillatory circuit, and determining a decay of said induced oscillation as said parameter directly related to dielectric polarization.

4. A method as claimed in claim 1 wherein the step of determining said at least one parameter directly related to dielectric polarization comprises determining a plurality of different parameters directly related to dielectric polarization to produce a plurality of measured values, and analyzing said anaesthetic agent dependent on all of said measured values.

5. A method as claimed in claim 1 wherein the step of determining at least one parameter directly related to dielectric polarization comprises determining a same parameter a plurality of different times to obtain a plurality of measured values, and analyzing said anaesthetic agent dependent on all of said measured values.

6. A method as claimed in claim 1 wherein said anaesthetic agent has an unknown identity, and wherein the step of analyzing said anaesthetic agent dependent on said measured parameter comprises identifying said anaesthetic agent dependent on said measured parameter.

7. A method as claimed in claim 1 wherein the step of analyzing said anaesthetic agent dependent on said measured parameter comprises comparing said measured parameter to a predetermined dielectric polarization template.

8. An analyzer for analyzing anaesthetic agents comprising:
    a measuring unit which measures a parameter directly related to dielectric polarization of an anaesthetic agent, to obtain a measurement result; and an analysis unit, supplied with said measurement result, for analyzing said anaesthetic agent dependent on said parameter.

9. An analyzer as claimed in claim 8 wherein said measuring unit comprises a first conductive surface and a second conductive surface, a voltage source in controlled connection to said first conductive surface and said second conductive surface to apply a voltage across said first conductive surface and said second conductive surface and to thereby generate an electrical field across at least a portion of said anaesthetic agent, and a voltmeter for measuring a voltage across said first conductive surface and said second conductive surface as said parameter directly related to polarization.

10. An analyzer as claimed in claim 9 further comprising a control unit for connecting said voltage source to said first conductive surface and to said second conductive surface at time periods of controllable duration, and wherein said voltmeter measures a residual voltage which is said parameter directly related to polarization.

11. An analyzer as claimed in claim 9 further comprising a short-circuiting circuit selectively connectable to said first conductive surface and to said second conductive surface for selectively short-circuiting said first conductive surface and said second conductive surface.

12. An analyzer as claimed in claim 9 wherein said measuring unit further comprises an inductive load connected to said first conductive surface and to said second conductive surface to form an oscillatory circuit, and a timer, and a control unit for controlling said voltage source to apply a selected number of voltage pulses across said first conductive surface and said second conductive surface, said timer measuring a decay time of said voltage across said first conductive surface and said second conductive surface, said decay time comprising said parameter directly related to polarization.

13. An analyzer as claimed in claim 12 wherein said control unit controls said voltage source to produce a single pulse.

14. An analyzer as claimed in claim 13 wherein said control unit controls said voltage source to produce a single square pulse.

15. An analyzer as claimed in claim 12 wherein said control unit controls said voltage source to produce a train of voltage pulses comprising a plurality of pulses at a frequency exceeding 30 MHz.

16. An analyzer as claimed in claim 15 wherein said control unit controls said voltage source to produce said series of pulses at a frequency exceeding 40 MHz.

17. An analyzer as claimed in claim 9 wherein said first conductive surface and said second conductive surface respectively comprise two capacitor plates, disposed with said anaesthetic agent between said capacitor plates.

18. An analyzer as claimed in claim 8 wherein said measurement unit obtains a plurality of measurement results for a same parameter directly related to polarization, and wherein said analysis unit analyzes said anaesthetic agent dependent on said plurality of measurement results.

19. An analyzer as claimed in claim 8 wherein said measurement unit obtains a plurality of measurement results respectively for different parameters directly related to polarization, and wherein said analysis unit analyzes said anaesthetic agent dependent on said plurality of measurement results.

20. An analyzer as claimed in claim 8 wherein said anesthetic agent has an unknown identity, and wherein said analysis unit identifies said anaesthetic agent dependent on said parameter.

21. An analyzer as claimed in claim 8 wherein said analysis unit compares said parameter to a dielectric polarization parameter template.

* * * * *